(12) United States Patent
Larsen

(10) Patent No.: US 7,992,780 B2
(45) Date of Patent: Aug. 9, 2011

(54) SECURE IDENTIFICATION OF DEPENDANTS

(75) Inventor: Steven Larsen, Cross Plains, WI (US)

(73) Assignee: EPIC Systems Corporation, Verona, WI (US)

( * ) Notice: Subject to any disclaimer, the term of this patent is extended or adjusted under 35 U.S.C. 154(b) by 0 days.

(21) Appl. No.: 12/833,359

(22) Filed: Jul. 9, 2010

(65) Prior Publication Data
US 2010/0280844 A1    Nov. 4, 2010

Related U.S. Application Data

(63) Continuation of application No. 11/734,601, filed on Apr. 12, 2007, now abandoned.

(51) Int. Cl.
*G06K 5/00* (2006.01)

(52) U.S. Cl. .......................... 235/380; 235/375; 235/487

(58) Field of Classification Search .................. 235/375, 235/380, 382, 487
See application file for complete search history.

(56) References Cited

U.S. PATENT DOCUMENTS

2007/0005403 A1 *   1/2007   Kennedy et al. .................. 705/4

* cited by examiner

*Primary Examiner* — Karl D Frech
(74) *Attorney, Agent, or Firm* — Quarles & Brady LLP

(57) ABSTRACT

The present invention provides a method for identifying patients using common forms of identification, and specifically readable personal identifiers such as credit cards, and for identifying dependents through a guardian's personal identification. The guardian registers the account with a health care database, and associates the dependent patients with the account. Thereafter, the guardian can process healthcare services for the guardian by providing a readable identifier identifying the account. As a result, the guardian can register the dependent patient for an appointment through a kiosk or other publicly accessible terminal, and can also access scheduling or other services.

27 Claims, 18 Drawing Sheets

Fig. 5

| Patient | Card ID | Cardholder | Relationship | ID | Pay | Co | Identifier |
|---|---|---|---|---|---|---|---|
| Bruce Johnson | MC xxxxxx1880 | Bruce Johnson | Self | Y | Y | N | YYYYY |
| Bradley Johnson | | | | | | | |
| Elizabeth Johnson | | | | | | | |
| SallySmith | | | | | | | |
| ... | | | | | | | |

Fig. 6

| Patient | Card ID | Cardholder | Relationship | ID | Pay | Co | Identifier |
|---|---|---|---|---|---|---|---|
| Bruce Johnson | MC xxxxxx1880 | Bruce Johnson | Self | Y | Y | N | YYYYY |
| Bradley Johnson | MC xxxxxx1880 | Bruce Johnson | Dependent | Y | N | N | YYYYY |
| | MC xxxxxx1880 | Helen Smith | Dependent | Y | Y | Y | YYYZZZ |
| Elizabeth Johnson | MC xxxxxx1880 | Bruce Johnson | Dependent | Y | N | N | YYYYY |
| SallySmith | MC xxxxxx1880 | Helen Smith | Dependent | Y | Y | N | YYYZZZ |
| ... | | | | | | | |

Fig. 6A

| Patient | Card ID | Cardholder | Relationship | ID | Pay | Co | Identifier |
|---|---|---|---|---|---|---|---|
| Bruce Johnson | MC xxxxxx1880 | Bruce Johnson | Self | Y | Y | N | YYYYY |
| Bradley Johnson | VS xxxxxx1996 | Bruce Johnson | Dependent | Y | N | N | YYYNNN |
| | MC xxxxxx1334 | Helen Smith | Dependent | Y | Y | N | YYYZZZ |
| Elizabeth Johnson | VS xxxxxx1996 | Bruce Johnson | Dependent | Y | N | N | YYYYY |
| SallySmith | MC xxxxxx1334 | Helen Smith | Dependent | Y | Y | N | YYYZZZ |
| ... | | | | | | | |

150

Patient Data

| | | |
|---|---|---|
| Name: | Sally Smith | — 152 |
| SSN: | 666-66-6669 | — 154 |
| BD: | 1/5/99 | — 156 |
| Relationship To Cardholder: | Dependent | — 158 |

Add Identifier For Patient

| | | |
|---|---|---|
| Card Type: | Credit | — 162 |
| Card Brand: | MasterCard | — 164 |
| Card Number: | MCxxxxxx1880 | — 166 |
| Holder Name: | Helen Smith | — 168 |
| Expiration: | 5/09 | — 169 |

Fig. 9

| Patient | Guardian | Guardian | SSN |
|---|---|---|---|
| Bruce Johnson 555 Maple Drive Springfield | Self | | 666-66-6666 |
| Elizabeth Johnson 555 Maple Drive Springfield | Bruce Johnson Same | Helen Smith | 666-66-6667 |
| Bradley Johnson 555 Maple Drive Springfield | Bruce Johnson Same | Helen Smith | 666-66-6668 |
| Sally Smith 777 Oak Court Springfield | Helen Smith 555 Maple Drive Springfield | Bob Smith | 666-66-6669 |
| ... | | | |

Fig. 11

| 292 | 293 | 294 | 295 | 296 |
|---|---|---|---|---|
| Patient | Birthdate | SSN | Phone | Zip |
| Bruce Johnson 555 Maple Drive Springfield | 07/31/1960 | xxx-xx-6666 | xxx-7777 | 54321 |
| Bruce Johnson 555 Maple Drive Springfield | 05/01/1937 | xxx-xx-6667 | xxx-7777 | 54321 |
| Bruno Johnsrud 1222 North St. Springdale | 06/03/1979 | xxx-xx-6666 | xxx-7788 | 54322 |
| Bruce Johnstone 777 Oak Court Springfield | 06/04/1979 | xxx-xx-6667 | xxx-6583 | 54333 |
| ... | | | | |

Fig. 23

SECURE IDENTIFICATION OF DEPENDANTS

CROSS-REFERENCE TO RELATED APPLICATIONS

This application claims priority to and is a continuation of U.S. patent application Ser. No. 11/734,601, filed Apr. 12, 2007 now abandoned, which is hereby incorporated by reference in its entirety.

STATEMENT REGARDING FEDERALLY SPONSORED RESEARCH OR DEVELOPMENT

N/A

BACKGROUND OF THE INVENTION

In recent years, kiosks and other types of automated registration and check-in devices have become commonplace for registering for flights at airports. In these automated check-in devices, a credit card or other personal identification card, such as a driver's license, is typically inserted into a card reading device. A computer reads the personal data provided on the magnetic strip, and compares the data to data stored in a database of, for example, flights and associated passengers. If the personal data matches the passenger data, the passenger is automatically checked in, thereby limiting the need to stand in long lines to register for flights. Similar systems have been developed for hotel check-in, registration at trade shows, accessing tickets for athletic events and theaters, and elsewhere where check-in or registration for a limited number of seats or times is necessary. More recently, this technology has also been expanded to include registration or check-in services in hospitals and health care facilities.

While many such systems exist, however, these systems have somewhat limited functionality because registration can be limited to those who have the appropriate form of identification, typically a credit card. Therefore, families with children, for example, typically cannot register using automatic check-in services, because the children do not have credit card forms of identification. Furthermore, these systems typically do not require any verification of the identity of the user. These problems are particularly acute in the health care industry, where it is important to accurately identify the patient, and to quickly and easily process the registration of a sick child. The present invention addresses this problem.

BRIEF SUMMARY OF THE INVENTION

The present invention provides a secure system and a method for correlating the records of one or more dependents with a personal identifier of a guardian. In this method, at least one dependent, such as a child or another dependent person, is associated with the personal identifier of a guardian, such as a parent or other care-giver, in a database. The personal identifier can be a common form of identification such as a credit card, driver's license, insurance card or other form of identification, or a token generated specifically for use in this application. Except for purposes of supplying the personal identifier, the guardian is not required to be otherwise associated with the health care or database system. Based on the personal identifier, the guardian is granted certain access to the associated dependent's records. Such access may include permitting the guardian to check the dependent in for an appointment, schedule or reschedule an appointment for the dependent, or to view or modify the dependent's personal information.

In one aspect of the invention, a method is provided for correlating dependent patients with a personal identifier of a guardian in a health care system for checking into an appointment or accessing health care records. The method comprises the steps of obtaining a readable personal identifier from a guardian of a dependent patient, registering the readable personal identifier with the dependent patient in a healthcare database, and prompting a user to present the readable personal identifier to a reader at a health care facility. When the user presents the readable identifier at the healthcare facility, the guardian is provided access to process health care or related services for the dependent patient.

In another aspect of the invention, the readable personal identifier comprises a credit card, a driver's license, a health insurance card, or a personal identification card. In another aspect of the invention, a unique identifier can be provided as a combination of information, such as an account number associated with the credit card and a cardholder name, and a first and a second cardholder can be associated with a first and second unique identifier. A first dependent, moreover, can be associated with the first unique identifier and a second dependent patient with the second unique identifier. Therefore, by way of example, two individuals who share a credit card account can have access rights for different individuals or sets of individuals.

In another aspect of the invention, a kiosk including a reader capable of reading the personal identifier is provided, and is programmed to compare the personal identifier to the data in the healthcare database and to display at least one dependent associated with the personal identifier at check-in.

In another aspect of the invention, the personal identifier comprises at least one of a biometric identifier, an active memory storage device and a passive memory storage device. Alternatively, the personal identifier can comprise any of a number of different types of readable tokens.

In still another aspect of the invention, a data access system is provided for use in a health care facility. The data access system includes a health care computer network, a health care database including a patient database, and a data structure associating a readable personal identifier of a guardian with at least one dependent patient. A reader device is connected to the computer network for reading the readable personal identifier when presented. When the identifier is read, the computer network is programmed to correlate the readable personal identifier with the dependent patient in the database and to provide the guardian access to at least a portion of the health care database to process health care services for the patient.

In another aspect of the invention, the data access system provides the guardian access to check the dependent patient in for an appointment or to schedule an appointment for the patient.

In yet another aspect of the invention, the readable personal identifier comprises at least one of a credit card, a driver's license, a health insurance card, an active memory storage device, a passive memory storage device, and a biometric identifier.

In still another aspect of the invention, the reader is provided in a kiosk connected to the computer network and providing a display for interacting with the guardian and the dependent patient.

In a further aspect of the invention, a method is providing for associating dependent patients with first and second holders of a single account. In this method, a first account holder is prompted to register account data in a healthcare database, the account data including at least one of an account number and an identifier of the first account holder. A second account holder is also prompted to register account data in the healthcare database, the account data including at least one of the account number and an identifier of the second account holder. A dependent of the first accountholder is then associated with the first accountholder in a database; and a dependent of the second accountholder is associated in a database with the second accountholder, wherein when the first accountholder uses the account as identification, the first accountholder is provided access to process health care services for the first dependent and when the second accountholder provides a credit card associated with the account as identification, the second accountholder is provided access to process health care services for the second dependent. In another aspect of the invention, the system can produce a first unique identifier as a combination of the account number and identification of the first accountholder. A second unique identifier can be produced as a combination of the account number and identification of the second accountholder. Additionally, an individual can be associated with both account holders so that either the first or second account holder is provided access to process health care services for the individual.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

BRIEF DESCRIPTION OF THE DRAWINGS

FIG. 5 is a graphic illustration of a database providing correlation of patient data to identification data prior to the addition of identifying data;

FIG. 6 is a graphic illustration of the database of FIG. 5 with patient identification data registered to the database;

FIG. 6A is a simplified block diagram showing a data access system implementing the secure identification method;

FIG. 8 is a screen shot of a screen used by a receptionist to enter patient data for lookup;

FIG. 9 is a screen shot illustrating the process of adding an identifier for the patient;

FIG. 11 is an illustration of a guardian/dependent correlation database;

FIG. 23 is a schematic illustrating a patient database for use with a patient look-up;

DETAILED DESCRIPTION OF THE PREFERRED EMBODIMENT

Figure 1:
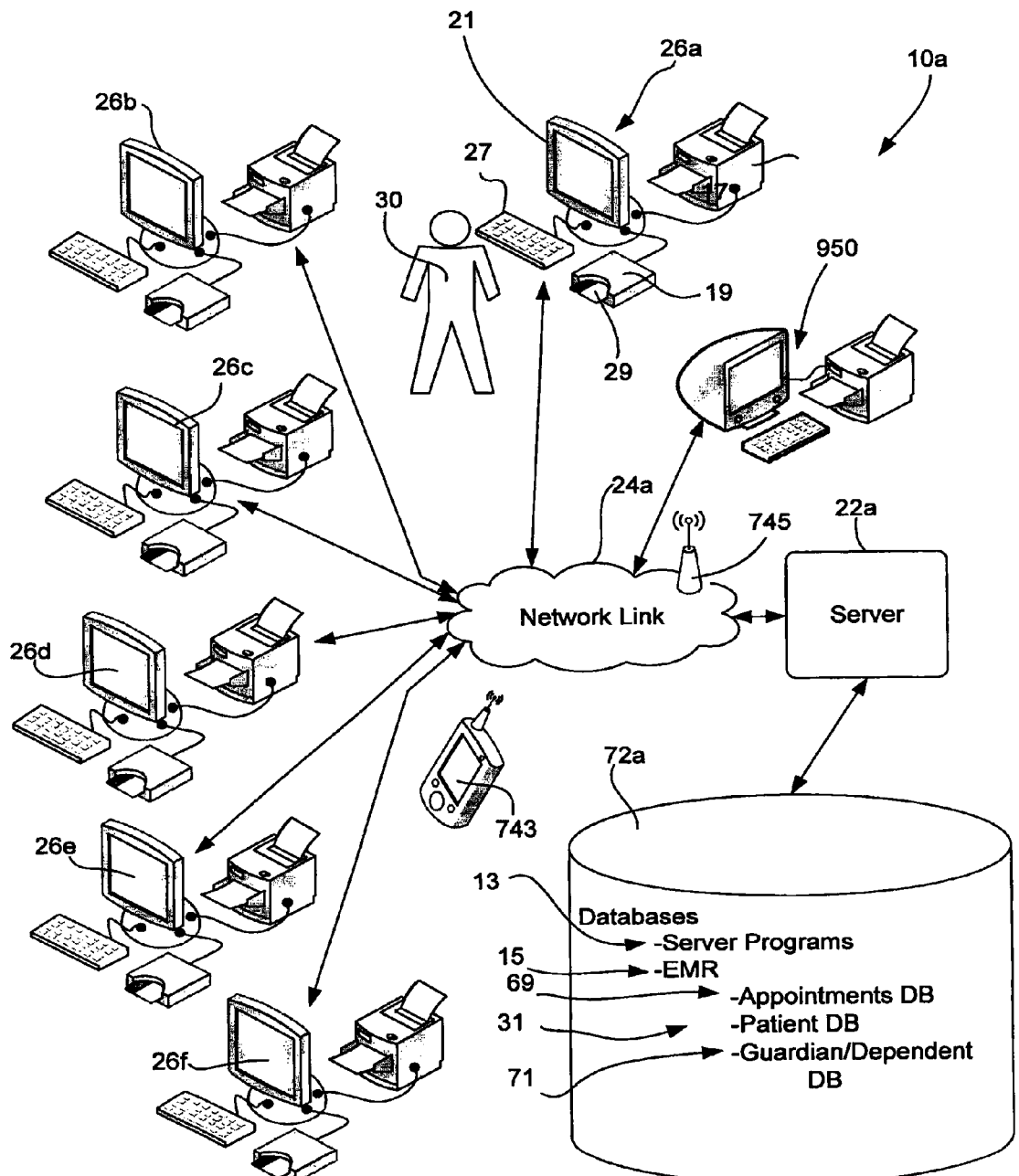
FIG. 1 is a schematic illustration of a health care computer system including a plurality of kiosks for patient check-in and other uses.

Referring now to the figures, and more particularly to FIG. 1, an exemplary patient check-in system 10a is shown including a server 22a, memory storage 72a, a network 24a (e.g., a local area network, a wide area network, the Internet, etc. which may include wireless transceiver or transceivers 745), a receptionists station 950, and a plurality of patient kiosks 26a, 26b, 26c, 26d, 26e and 26f. Server 22a runs software programs that perform various methods/processes that are contemplated by the present invention and to provide browser type screen shots to the kiosks 26a, 26b, etc., and to receive input from the kiosks. Each of kiosks 26a, 26b, etc., may take any of several different forms including work stations, personal computers, laptops, thin-client type devices, etc. Where the kiosks are more than thin clients, in at least some embodiments each kiosk may perform all or at least a subset of the steps required to perform the inventive processes. When the kiosks are thin client type devices, each kiosk operates primarily as a human-server interface device for input/output between a patient and server 22a where server 22a performs most or all of the inventive process steps. Hereinafter, unless indicated otherwise and in the interest of simplifying this explanation, it will be assumed that each kiosk 26a, 26b, etc., is a thin client type device.

Each of the kiosks 26, 26b, etc., is similarly constructed and operates in a similar fashion and therefore, in the interest of simplifying this explanation, only kiosk 26a will be described here in any detail. Kiosk 26a includes a flat panel display 21, an input device 27, a card reader 19 and a printer 17. Input device 27 is shown as a keyboard but may include other input devices such as a mouse device, a track ball type device, etc., and, is generally provided for, as the label implies, entering information into system 10a for use by server 22a. In the present case it will be assumed that the input device(s) 27 includes a keyboard for entering text type information and a mouse type device (not illustrated) for moving a mouse controlled cursor (see 351 in FIG. 13) around on the screen of display 21. Furthermore, the display 21 may be a touch screen display. In this application, therefore, the touch screen provides the function of the input device 27.

Card reader 19 includes a slot for receiving identification cards from patients for identification purposes. In this regard, the identification card may be a credit card, a driver's license, a dedicated insurance card, a healthcare card, etc., from which information can be read to uniquely identify a cardholder. The cardholder can be either a patient, a guardian of a patient, or both, and is not required to have any other relationship with the database system except with regards to the personal identifier. When the cardholder is a guardian, the cardholder can access the kiosk system to check in an associated dependent for an appointment, as described below. In addition, through use of the associated patient identifier, the cardholder can access records associated with the dependent. To this end, prior to using one of the kiosks to check-in for an appointment it is contemplated that patient identities will be associated with patient unique cards in one or more database in memory storage 72a, as described more thoroughly below.

Memory storage 72a is linked to server 22a and stores programs 13 performed by server 22a and various data arranged in data structures and databases (also referred to as "databases" hereinafter) that may be used by the server software to perform inventive methods. To this end, memory 72a includes an electronic medical records database 15 that, as the label implies, stores electronic medical records (EMRs) for facility patients. While EMRs often are extremely detailed, for the purposes of this disclosure portions of the EMR are particularly important. To this end, as shown in FIG. 1, EMR database 15 includes a patient identification database 31, an appointments or scheduling database 69, and a guardian/dependent database 71. Here, while each of databases 31, 69 and 71 are referred to as separate databases in the interest of simplifying this explanation, is should be appreciated that, in at least some cases, each database 31, 69, and 71 may in fact include data interspersed among separate patient EMRs, and may include data that is stored outside of an EMR database 15. The databases described herein are merely provided as an example, and the data is shown arranged in a manner intended to simplify explanation of the invention. It will be apparent to those of ordinary skill in the art that the data can be arranged in any of a number of different ways, in one or multiple databases, and that the description here is not intended to limit the invention.

The present invention provides methods for identifying patients using common forms of identification, and, in a specific example, readable personal identifiers such as credit cards, and for identifying dependents through a guardian's personal identification. By way of example, the system will be described with reference to an exemplary family, headed by Bruce Johnson and his wife Helen Smith. Bruce and Helen are the parents of Bradley Johnson. Bruce has a daughter, Elizabeth Johnson, from a previous marriage, and Helen has a daughter, Sally Smith, from a previous marriage. Bruce, Bradley and Elizabeth Johnson are all patients at St. Daniel's clinic, as is Sally Smith. Helen Smith is not a patient, and is not identified in the associated databases in memory 72a. Registration of the extended Johnson family using registered personal identifiers and particularly through a patient check-in system 10a is described below. Registration is shown through a series of exemplary screen shots. It will be apparent, however, that the form of data entry can be varied and that these screen shots are provided by way of illustration only.

Moreover, as the present invention is shown for a kiosk system, it will be apparent that the invention can also be used with other systems that use personal identifiers and identification cards to identify users.

Figure 2:
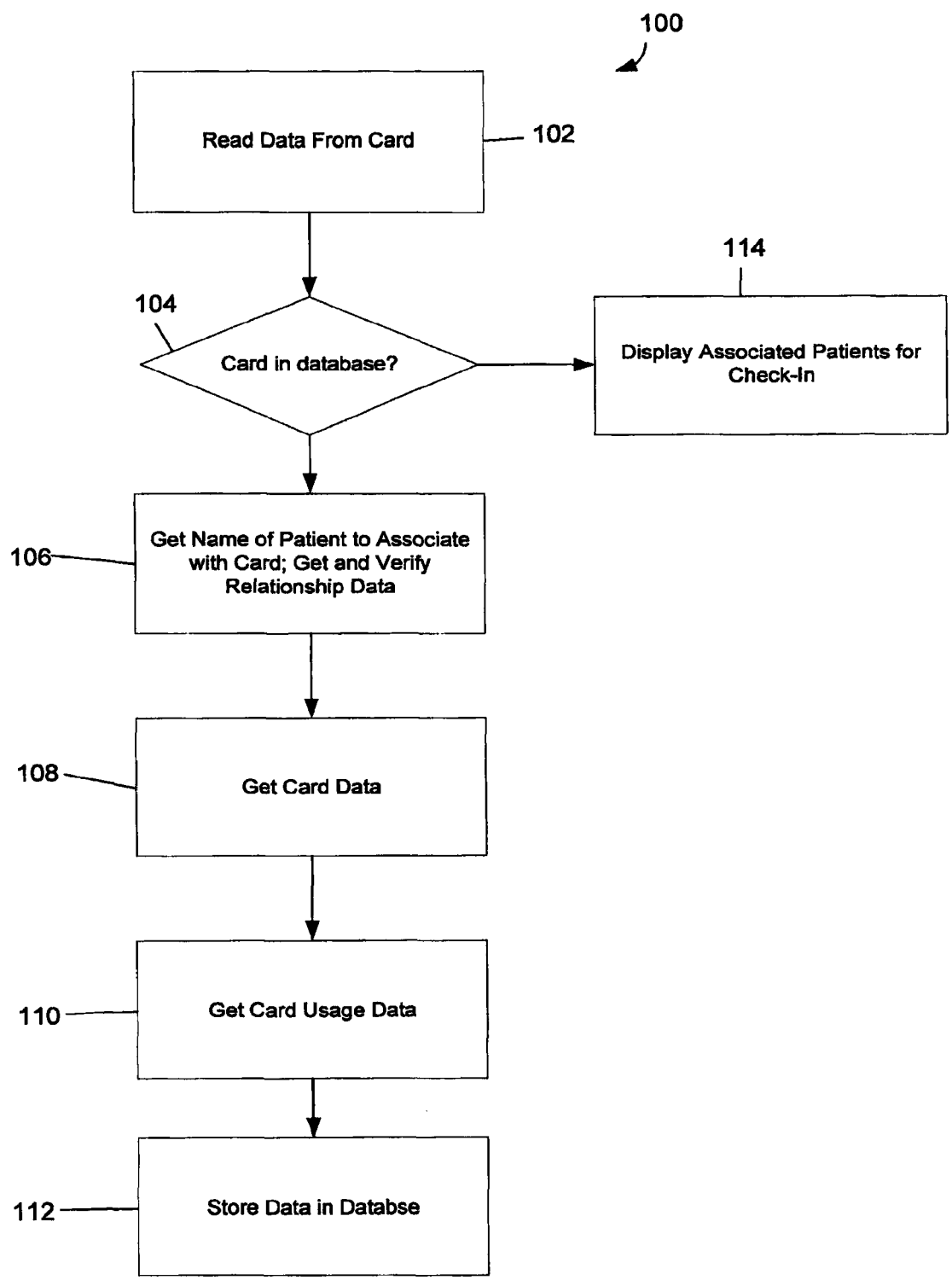
FIG. 2 is a simplified flow chart showing the method of the present invention for registering dependents with guardian identification.

Referring now to FIG. 2, a flowchart showing a process 100 for correlating one or more patients with a personal identifier is shown. As described here, the process will initially be described for providing a personal identification card for Sally Smith, the daughter of Helen Smith, who, as noted above, is not a patient at the clinic. Subsequently, a similar process will be shown for Bruce Johnson, who is a patient of the clinic, registering his daughter Elizabeth, from a kiosk 26a. Both Helen and Bruce will also register their son, Bradley. In this example, it is assumed that Bruce and Helen share a credit card account and use this credit card account MC xxxxxx1880 to register the dependent patients.

Figure 3:
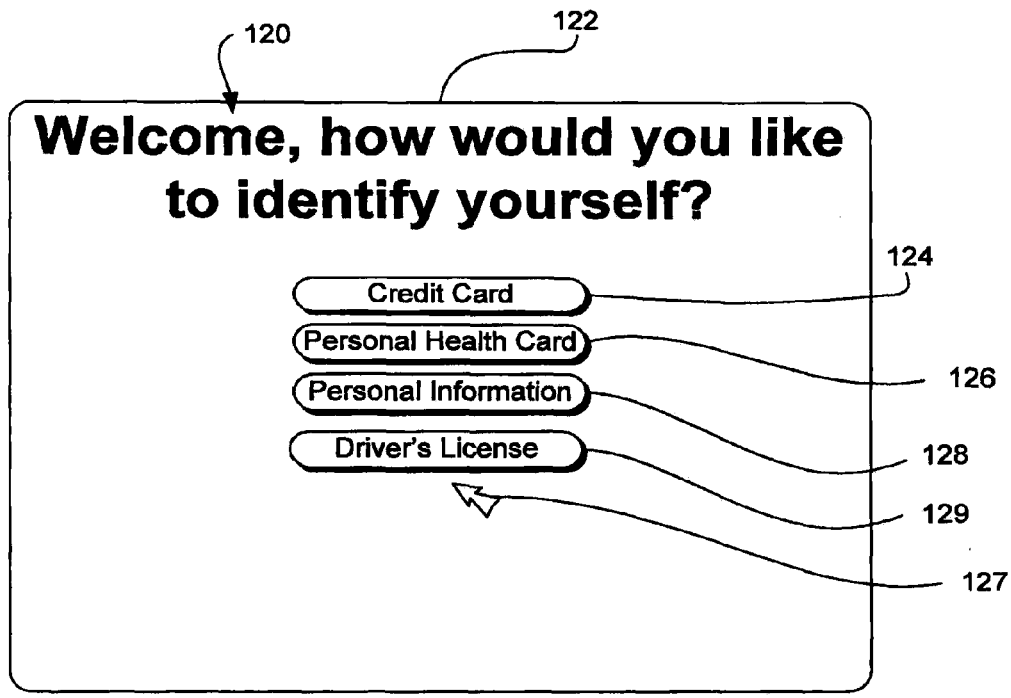
FIG. 3 is a screen shot illustrating a welcome screen when entering a health care facility.
Figure 4:
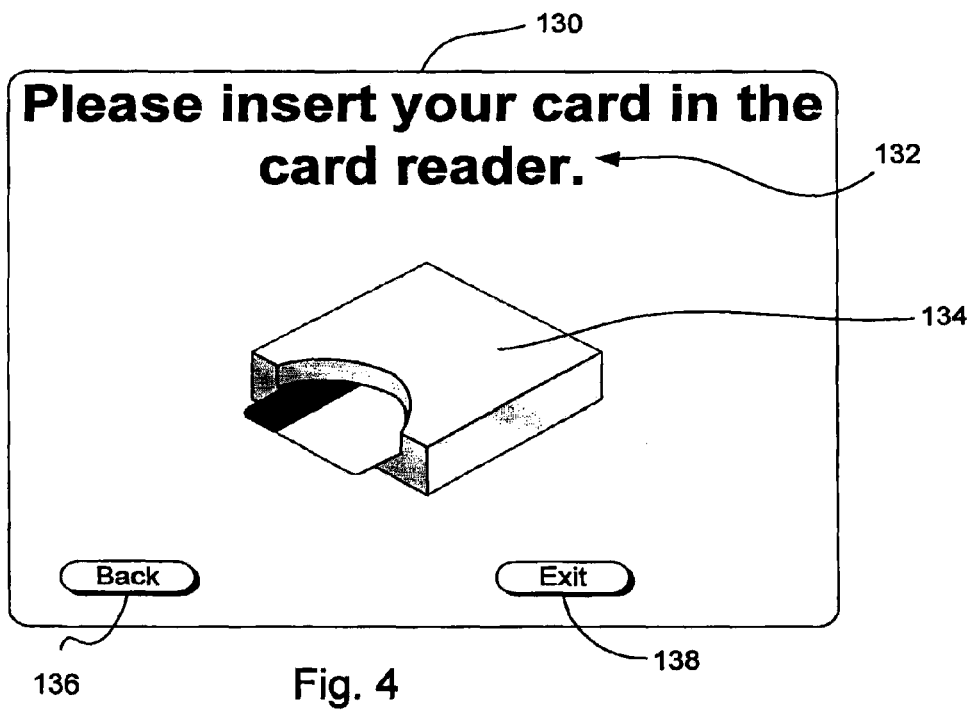
FIG. 4 is a screen shot illustrating an "insert card" screen.

Referring still to FIG. 2 and also to FIGS. 3 and 4, when Helen Smith approaches the kiosk 26a upon entry to the clinic, a screenshot 120, welcoming a user to the kiosk 26a is shown. At screenshot 120, a message 122 is provided asking the user to identify his or her self. Selectable icons are also provided for entering a personal identifier, which can be a credit card 124, personal health card 126, personal information 128, or a driver's license 129, as shown here, or various other forms of identification and other types discussed hereafter. An arrow 127 can also be provided to select between the icons. Although any of these various types of identification can be used in the present invention, in the description below, it will be assumed that the identification provided is a credit card having account number MC xxxxxx1880.

Figure 7:
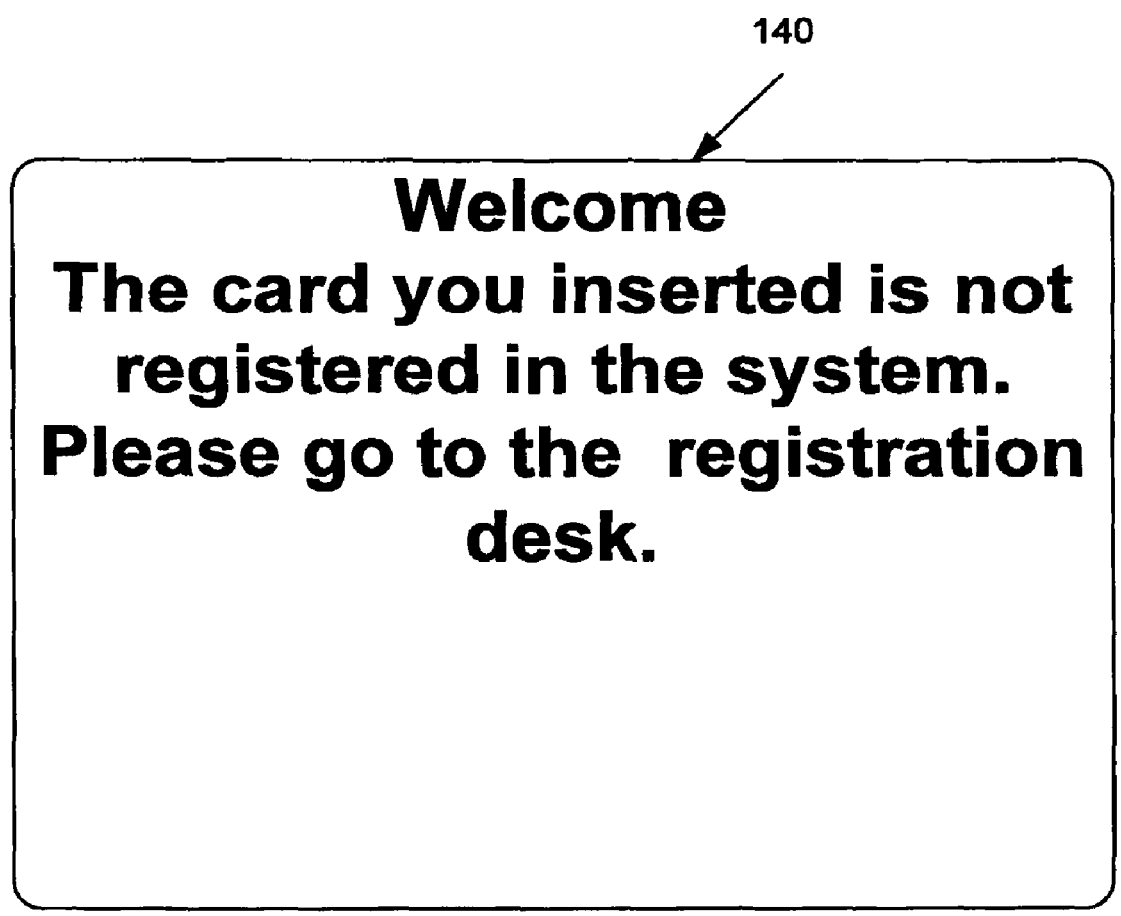
FIG. 7 is a screen shot illustrating an instruction to register an identification card with a receptionist.

Referring now to FIG. 4, after Helen Smith chooses to insert a credit card using icon 124, screenshot 130 is displayed, including a message 132 instructing the user to insert the card in a card reader 19, shown schematically as card reader 134. Icons providing options to return to the last screen 136 and to exit the process 138 are also provided. Referring now also to FIG. 5, in process block 104 of FIG. 2, an identity of the cardholder and the card number are retrieved from the magnetic strip on the card, and the card data is evaluated as compared to data in database 31. Because neither the card nor Helen Smith is found in the database, either as a patient, guardian, or as a cardholder, screen shot 140 is displayed (FIG. 7), instructing Helen Smith to proceed to the registration desk 950 to register the card in accordance with the steps provided below.

Figure 10:
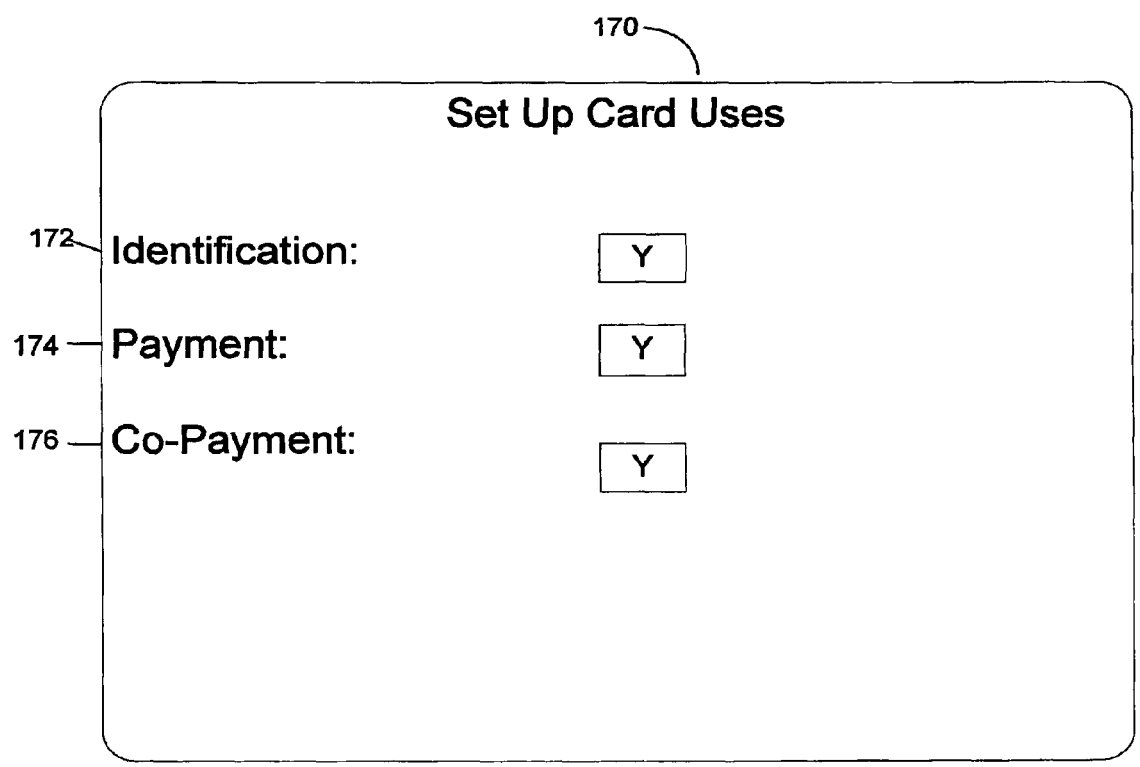
FIG. 10 is a screen shot illustrating a set-up of card usage.

Referring still to FIGS. 1, 2, 5, and now to FIGS. 8-10, to associate a patient with the card, in process block 106, the receptionist or other personnel requests identification data for the patient or dependent that is to be registered with the card, and enters this data into a patient data screen 150. In this screen, the name of the patient, Sally Smith, is entered in block 152, along with a social security number in block 154, and a birth date in block 156. The receptionist also requests verification of the relationship between the cardholder Helen Smith, and the patient Sally Smith, and, after verification, enters this relationship into data block 158. The process 100 then compares the entered data to data in the EMR database 15, and verifies the identity of the patient. When an appropriate relationship is established and verified by the receptionist, the process proceeds to process block 108, and the receptionist acquires credit card data from Helen Smith. The relationship data may also optionally be stored in a guardian/dependent database 71, as described below.

Referring now also to FIG. 9, the receptionist next acquires credit card data including the type of card 162, brand of card 164, card number 166, cardholder name 168, and expiration date 169. The data is entered by the receptionist into screenshot 160. When the identification is a credit card as described here, the card can be used both for identification and for payment purposes, and the receptionist therefore requests information regarding how the card is to be used, as shown in screen shot 170 of FIG. 10, which provides the options of identification 172, payment 174, and co-payment 176. After the appropriate data is acquired, the data is entered into the screen shot 170. Although a limited number of options are shown here by way of example, it will be apparent that card usage can include additional options, and that these options can be specified by the facility. For example, it is also possible to specify whether the card is to be used solely for check-in, for scheduling of appointments, or for other types of health care access. These options can be individually configures by users or facilities. It will also be apparent that the type of data entered will vary depending on the type of identification card used. Thus, for example, the data entered for a driver's license will be specific to this form of identification.

Referring now also to FIGS. 5 and 6, a patient information database 51 is shown both prior to registration of identification cards, and after registration of identification cards, respectively. As shown in FIG. 5, therefore, initially, no identification data is associated with patient Sally Smith in column 80. After data is acquired in process block 112 (FIG. 2), the acquired data is stored to the database 31 for later retrieval. As shown in FIG. 6, the stored data can include patient name Sally Smith in column 80, card identification number MC xxxxxx1880 in column 82, and the card holder name, Helen Smith, in column 84. A relationship between the cardholder and identified patient is stored in column 86, and card usage data is stored in columns 88 and 90. When the card data is stored to the database 31, a patient identifier that can include a combination of card data and other identifying data associated with the card, such as a name of the cardholder, can be calculated or established, as described more fully below. This identifier can also be used to allow multiple users of a single credit card account to associate different patients with the account, also as described more fully below.

The relationship between Helen and Sally Smith can also be stored in the guardian/dependent database 71, as shown here in FIG. 11. When a guardian or caregiver is associated with a patient in the database, moreover, a level of access can also be established. For example, a parent may be allowed access to schedules and personal identification cards, and medical records of the specified dependent, while a caregiver such as a nanny or babysitter may be allowed access only to check in and out of scheduled appointments. For purposes of this example, it is assumed that, with the registration of Sally Smith, Helen Smith also registers her second dependent, Bradley Johnson, using the same credit card, as shown in database 31 of FIG. 6.

Although the correlation of identification cards to patients can be performed by a receptionist at reception desk 950, in alternate embodiments of the invention, a cardholder guardian can establish a secure means for identification of a dependent through the kiosk 26*a* as well, as will now be described as Bruce Johnson registers his dependents through the kiosk 26*a*. Referring again to FIG. 3, upon entry to the clinic, a screenshot 120, welcoming a user to the kiosk 26*a* is shown. At screenshot 120, a message 122 is again provided asking the user to identify his or her self and providing selectable icons for a credit card 124, personal health card 126, or personal information 128, or a driver's license 129. Although any of these various types of identification can be provided, in the description below, it will again be assumed that the identification provided is a credit card, and that the account number is MC xxxxxx1880.

Figure 12:
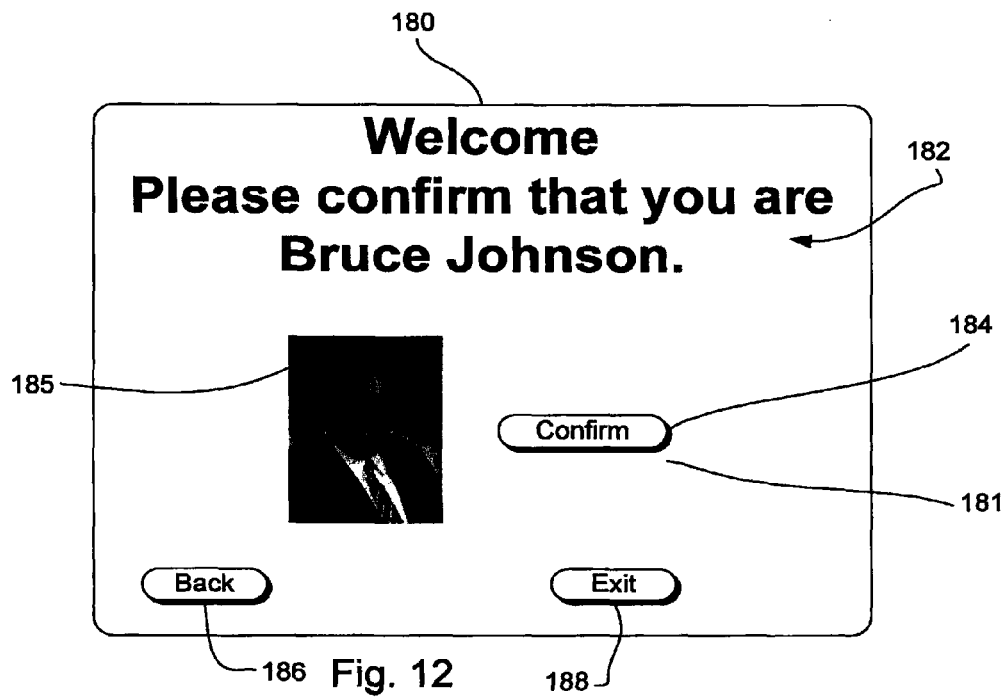
FIG. 12 is a screen shot of a welcome screen for a patient registering at a kiosk.

Referring now to FIG. 4, screenshot 130 is displayed next, providing a message 132 instructing the user to insert the card in a card reader 19, shown schematically as card reader 134. Referring now also to FIG. 12, the card reader 19 reads the data from the credit card, compares the data to the database 31 of FIG. 5, and recognizes both the name Bruce Johnson and the card as having been previously registered in database 31. Thereafter, a confirmation screen 180 can be provided asking the user in message 182 to confirm his or her identity by accessing the confirm icon 184. A picture 185 of the user can also be provided. To affirm identity, or as an alternative to the card insertion, the patient look-up process described below with reference to FIGS. 22-29 can also be used.

Figure 13:
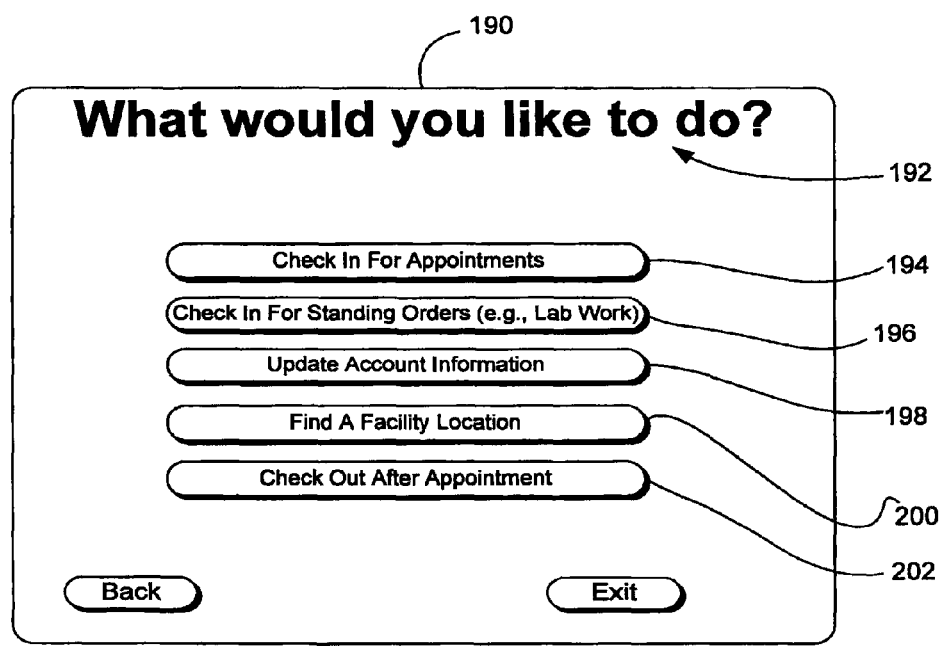
FIG. 13 is a screen shot of a selection screen for selecting a kiosk activity.

After the user Bruce Johnson has accessed the system, in screenshot 190 of FIG. 13, he is asked to select between a number of different possible options from the kiosk 26*a*. As shown here, the user can check in for appointments in icon 132, check in for lab work in icon 134, update account information in icon 136, find a facility location in icon 138, and check out after an appointment icon 140. In order to add personal identifiers to the database for himself and his dependents, the user selects an update account information icon 136 and proceeds to screenshot 140, which asks Mr. Johnson to select between various types of data to edit. As shown here, the data can include personal data 142, insurance data 144, and/or an option to setup personal identifiers in icon 146. When the personal identifier setup icon 146 is selected, the user can select to setup accounts for the personal identifier already submitted or provide an additional card or identifier (screen shot not shown). If an additional identifier is provided, in screenshot 130 (FIG. 4), the user is prompted to insert an additional identification card for registration in the card reader 19.

Figure 14:
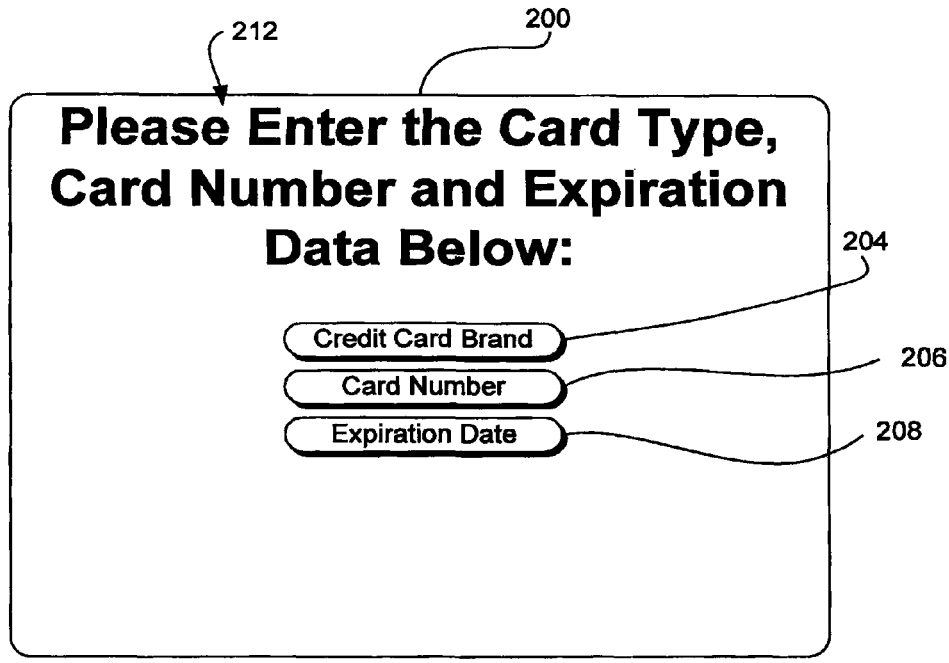
FIG. 14 is a screen shot for entering an identification card.

Referring now to FIG. 14, in addition to, or in lieu of entry of the card, the user can be prompted in screenshot 200 to enter the credit card brand 204, a card number 206, and the associated expiration date 208. After the card is identified and the acquired data is stored, server 22*a* accesses database 71 (FIG. 11), and retrieves a list of the patients associated with Bruce Johnson. As shown here, the database 71 includes a first column 60 of patient names, addresses and other identifiers; a second column 62 providing a first list of guardians; a third column 64 providing a second list of guardians and identifying data such as a social security number. Here, the database 71 identifies Bruce Johnson as a patient, and also identifies Bruce Johnson as the guardian of Elizabeth Johnson and Bradley Johnson. Helen Smith, due to the previous registration described above, can also be listed as a guardian. The system can, in order to provide additional security, also query the user to input a social security number, a portion of a social security number, a zip code or other identifying data to add a further level of security. Although a separate guardian/dependent database 71 is shown here, it will be apparent that the dependency data can also be provided in the database 31, as described above, or in any combination of logical or physical databases. The guardian/dependency relationships provided in the database 71 can be established either through entry of the data through a receptionist and receptionist computer 950, as described above, through pre-existing data in the database, by providing proof of guardianship to the clinic generally, through existing insurance or health care records, or in other ways which will be apparent to those of skill in the art.

Figure 15:
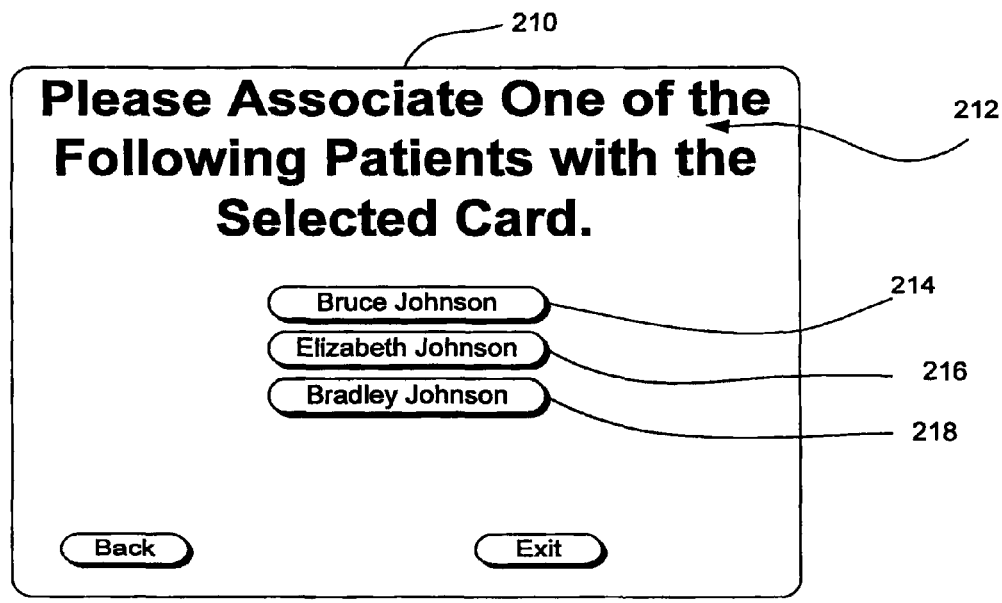
FIG. 15 is a screen shot for associating a patient with the identification card.
Figure 16:
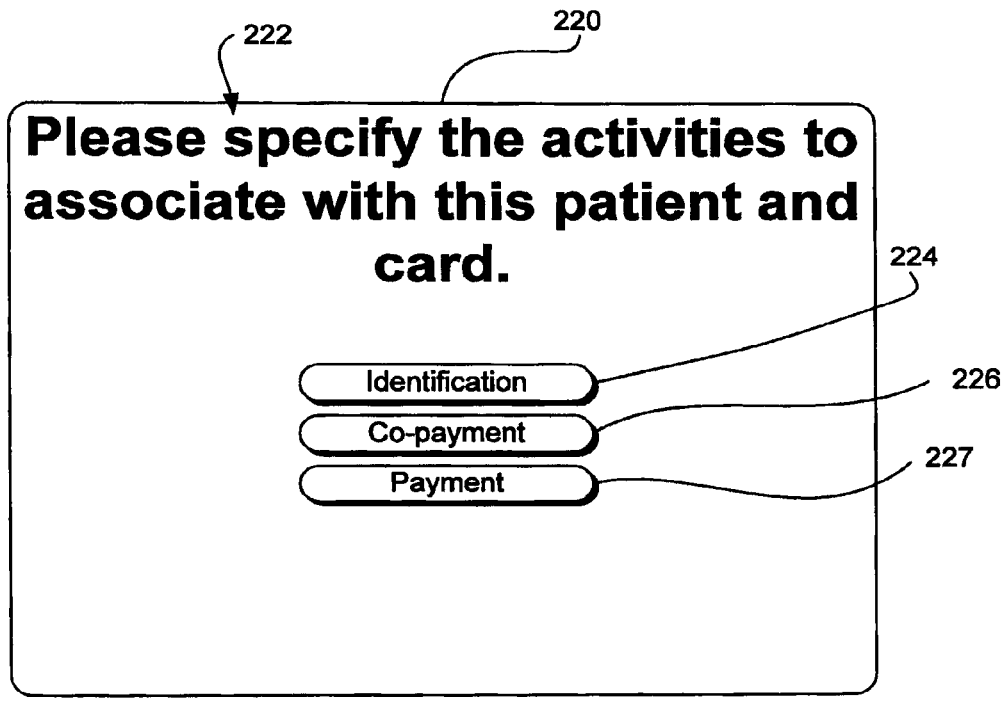
FIG. 16 is a screen shot illustrating identification of card usage through the kiosk.

Based on data retrieved from the database 71, screen shot 210 (FIG. 15) is displayed on the kiosk 26*a*, providing the names of the three patients that can be associated by Bruce Johnson—Bruce Johnson, Elizabeth Johnson, and Bradley Johnson—and the user Bruce Johnson is prompted to select a patient to associate with the card. Here it is assumed that Bruce Johnson selects Bradley Johnson. In screenshot 220 (FIG. 16), the system then requests the user to specify the activities that should be associated with the selected patient and card. When the identification is a credit card, as described here, the user can specify use for identification (icon 224) and for payment purposes, either for a co-pay only (icon 226) or payment for all purposes (icon 228). This data is then stored along with the card data and patient data in database 31. Various other data can also be manipulated and stored in the database 31, as will be apparent to those of skill in the art.

Figure 17:
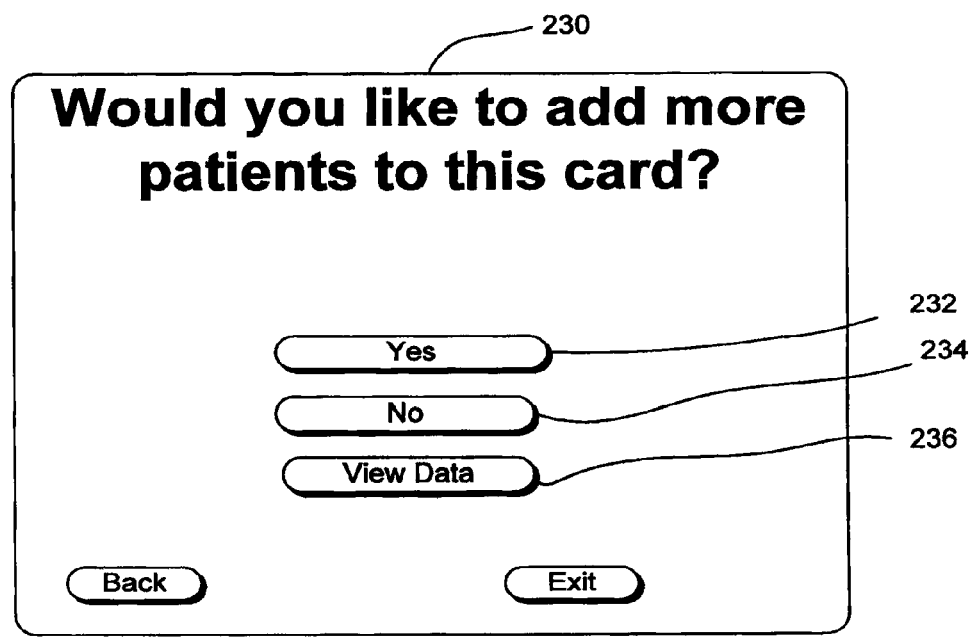
FIG. 17 is a screen shot illustrating the addition of additional patients to the card.

Referring now to FIG. 17, after the identification data is added to the card (screenshot 230), the cardholder is asked whether additional patients should be added to the card. Three icons appear. A yes icon 232, a no icon 234, and a view card data icon 236. Selecting the yes icon 232 returns the cardholder to screen 210 of FIG. 15, where Mr. Johnson can now register Bradley Johnson with his card, using the same steps specified above.

Figure 18:
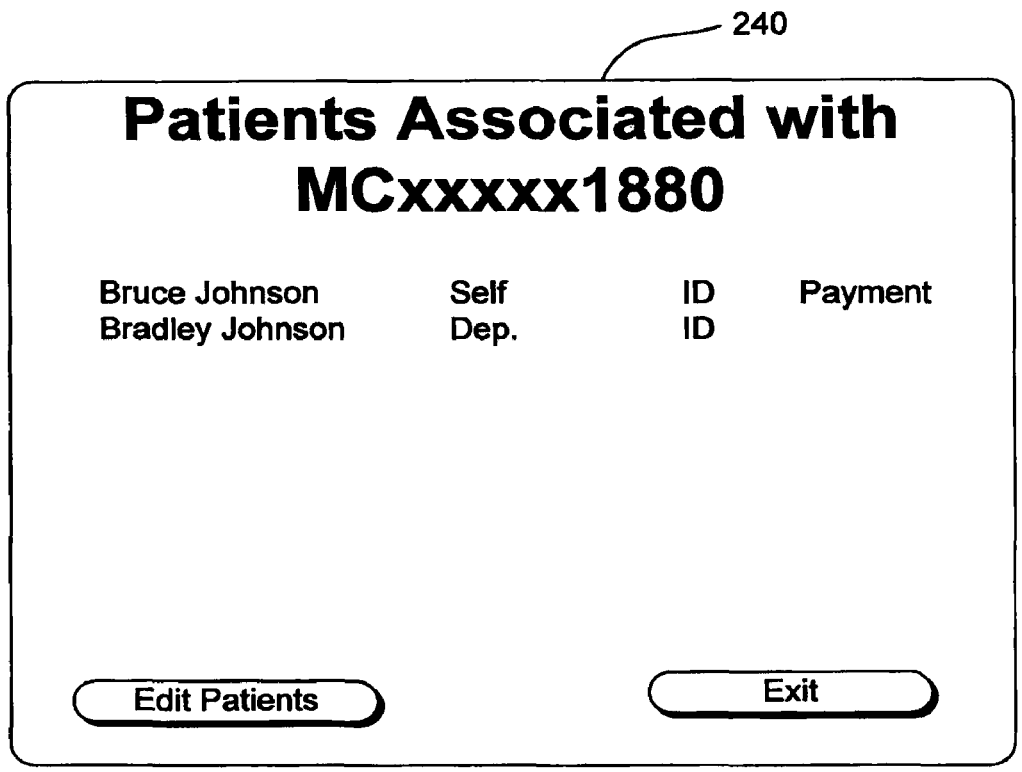
FIG. 18 is a screen shot illustrating review of the data associated with the card.
Figure 19:
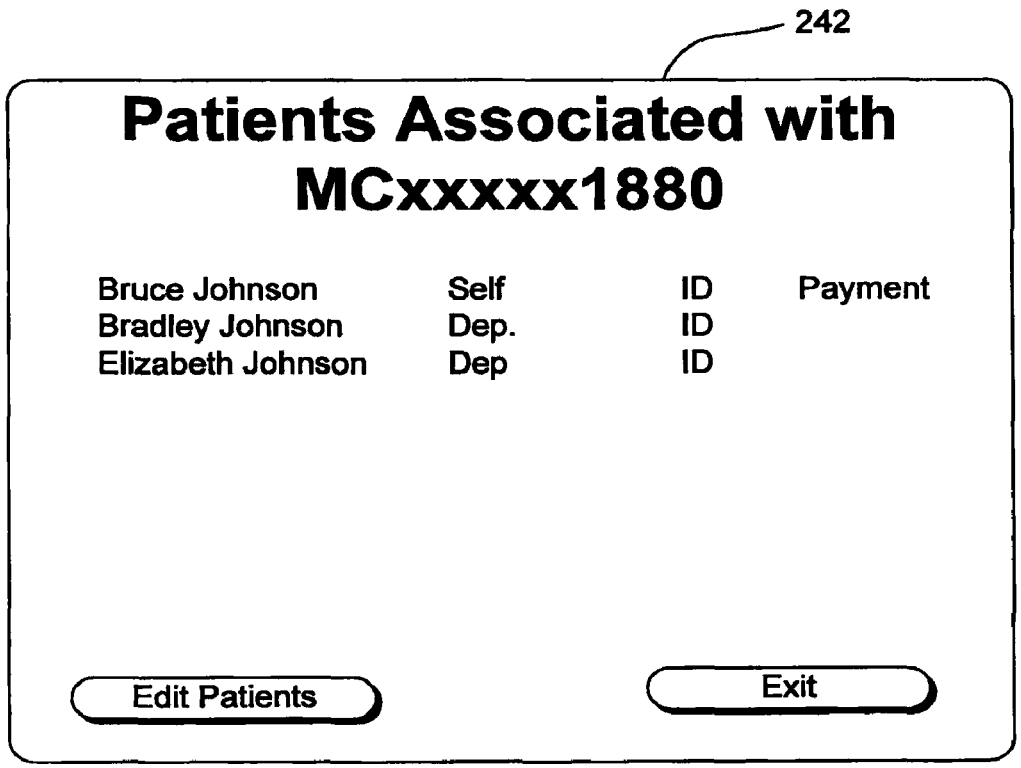
FIG. 19 is a screen shot illustrating review of the data associated with the card after an additional patient is added.

Selecting the no icon 234 takes the patient to screen 190 of FIG. 13 and selecting the view card data icon 236 takes the patient to screenshot 240 of FIG. 18, screenshot 240 where data from the database 31 is shown. At screenshot 240, a list of the patients associated with the registered card is shown. Bruce Johnson is listed as a patient, along with data specifying that the card is to be used both as identification and for payment. Bradley Johnson is also listed, as a dependent of Bruce Johnson. The card is used for identification only for Bradley. Referring now to FIG. 19, after the steps discussed above are also taken to add Elizabeth Johnson to the identification card, all three patients are registered to the card as shown in screenshot 242 of FIG. 19. Two additional icons, an "edit patients" icon 246 and an exit icon 248 are provided. When the patient chooses to exit by selecting icon 248, the kiosk screen returns to screenshot 190 of FIG. 13, which asks the patient what to do in message 192, and allows the patient to check in for appointments 194, check in for lab work 190, check in for standing orders 196, update account information 198, find a facility location 200, or checkout after an appointment 202. It will be apparent that the guardian can also be provided with options to schedule appointments, access medical records, or perform other health care procedures for the dependents. Furthermore, it will be apparent that, although an exit icon is shown here, various other screen and data flows are also possible.

Figure 20:
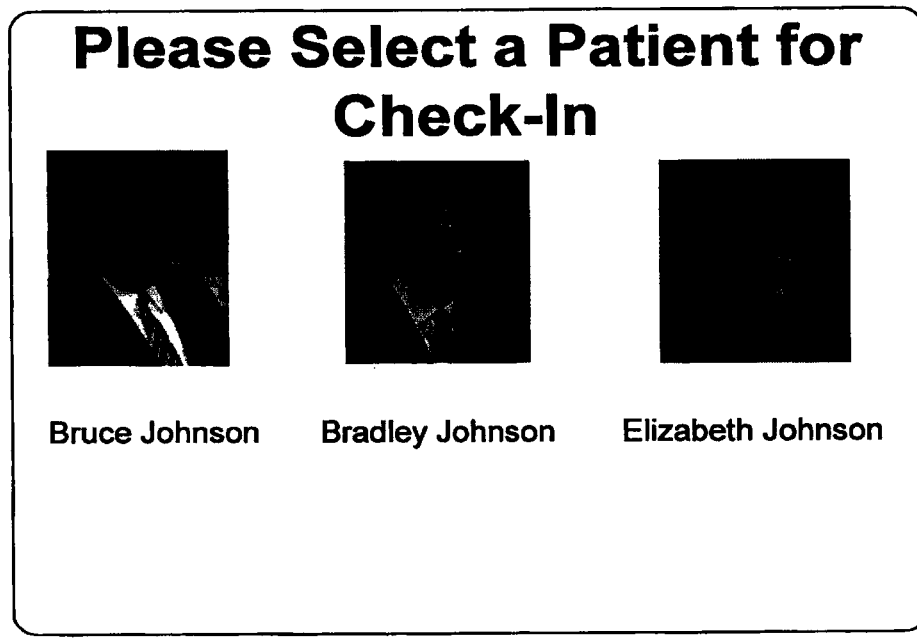
FIG. 20 is a screen shot illustrating the patients associated with a first identifier.
Figure 21:
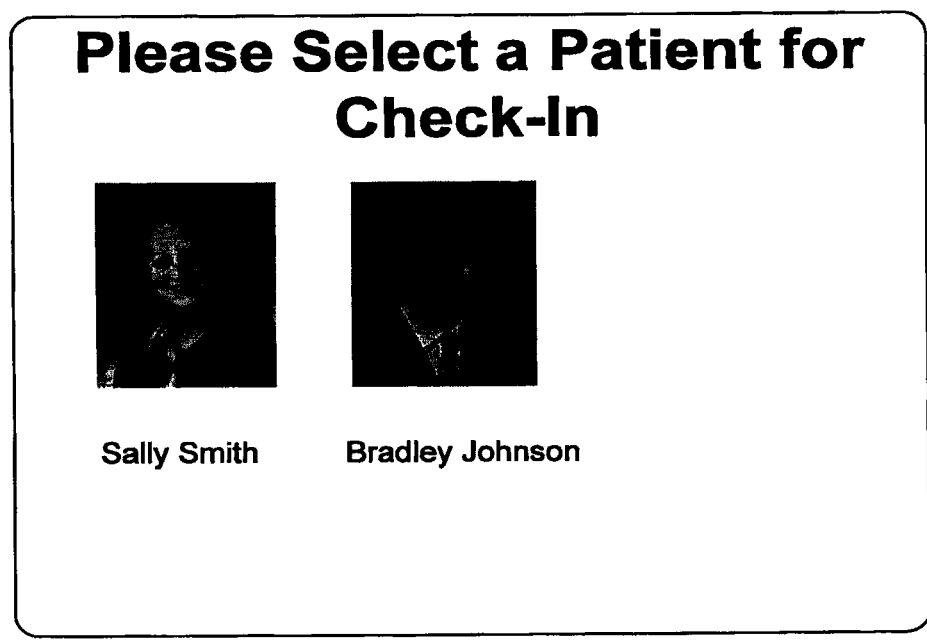
FIG. 21 is a screen shot illustrating the patients associated with a second identifier.

When the check in for appointments icon 194 icon is selected, screenshot 270 of FIG. 20 is displayed, illustrating Bruce Johnson, Elizabeth Johnson, and Bradley Johnson, and therefore all of the patients associated with the selected card and patient identification. When Helen Smith enters the facility and inserts her card with the same account number, her dependents Sally Smith and Bradley Johnson are shown (FIG. 21). Therefore, despite the fact that Bruce Johnson and Helen Smith are using the same credit account, they are provided with access to different sets of patients based on data retrieved from the database 31.

Referring again to FIGS. 5 and 6 and also to FIG. 6A, comparative exemplary databases are shown illustrating one implementation of the present invention. The database 31, as discussed above, correlates patients and personal identifiers here shown as identification cards. Referring first to FIG. 5, the database 31 includes a patient column 80, a card identification column 82, a cardholder column 84, a relationship column 86, an identification column 88, a payment column 90 and an identifier column 92. The patient column 82 includes the names of patients of the clinic, here providing the names of Bruce, Bradley and Elizabeth Johnson, as well as Sally Johnson. Helen Smith, as described above is not a patient. The remaining columns associate identification and payment information with the patients. In FIG. 5, no identification has been provided for any of the patients but Bruce Johnson, and these columns therefore are blank for the other listed patients.

FIG. 6 illustrates the database after Bruce Johnson and Helen Smith have registered their dependents in the database as described above, with both guardians using the same credit card account, which is shared by Helen Smith and Bruce Johnson. Here, although Bruce and Helen share the same credit card account, they do not share the same set of dependents, therefore another identifier is required to provide appropriate access to the parents. To account for this situation, a unique identifier, which can, for example, combine account data from column 82 and cardholder data from column 84 or any other identification data can be calculated and stored for each specific card as shown in column 92. As shown here, despite the fact that the same account is used, a first identifier is provided for the card when used by Bruce Johnson, and a second identifier for the account when used by Helen Smith. Thus, as shown in FIGS. 20 and 21, the same card can provide access to different sets of patients. Referring now to FIG. 6A, rather than using the same credit card as described above, the patients can be associated with different cards. Here, for example, Bruce Johnson uses credit card MCXXXXXX1880 to identify himself, and VSXXXXXX1996 to identify dependents Bradley and Elizabeth Johnson. Helen Smith uses a separate account, MCXXXXXX1334 to identify her dependents, Bradley Johnson and Sally Smith. Each parent, therefore, can associate their dependent children with different identification cards. Although a specific identifier is described in column 92, it will be apparent that the process can also determine the identity of the user by comparing a second form of identification, such as a name on the card, to data in the database, or require the insertion of a second form of identification from the parent, to differentiate between account holders rather than calculating a specific personal identifier shown in column 92. It will also be apparent that a patient can be associated with a number of different personal identifiers and cards, and that an unlimited number of patient identification associations can be established, stored, and maintained. Furthermore, it is also possible to identify cardholders based on the submitted identification card alone, or on the card in combination with personal data provided by the user.

As described above, in the preferred embodiment, the personal information is read from the magnetic strip of a credit card and stored in the database system as a database key. The personal information from the magnetic strip can be used to create a unique token, or can be compared to the stored data when entered. Although a credit card account number has been described above for simplicity, the token may also be a hash or other encrypted version of the account number of the credit card. In some applications, as in the situation described above where multiple users use the same credit card to identify different sets of patients, the database key requires more than the encrypted or hashed account number and might include any other identifying information available, such as the guardian's personal name, card id, the CV2 data, etc. thereby forming the identifier 92.

Although the system has been described above for simplicity as using a credit card for accessing data in the system, the personal identifier can be any type of readable personal identifier or token capable of storing unique identifying information and/or of being read by a machine. The personal identifier may, therefore, be a driver's license, insurance card, or health care identification card or a combination of such forms of identification, or any other form of identification that includes personal information such as account number, full name, address, date of birth, and telephone number stored in a machine readable format. The identifier may include active or passive memory storage, be an RFID tag, a barcode or other type of optical encoding device, or a biometric identifier.

As used herein, a dependent is a person that either does not have a useable personal identifier, or is not capable of using the personal identifier, such as a child or a dependent adult. The guardian can be any individual with a useable personal identifier, such as a parent or care-giver. The guardian, moreover, is not required to be otherwise associated in anyway with the health care facility or the database system. In the database system, the database record for the guardian's personal identifier can be associated with one or more database records of the dependents, with or without identifying the guardian.

Although specific database records are used by way of example above, it would be understood to one skilled in the art that the dependent's database record in the database system can take many forms, and may contain personal information of the dependent including without limitation name, address, date of birth, social security number, and sex. In addition, the method further contemplates one or more guardians each with their own personal identifier being associated with one or more identical dependents. In this situation, one or more guardians may take responsibility for the dependent, such as the case of parents. Further, the method contemplates a guardian with more than one personal identifier identifying the same or different dependents.

Figure 22:
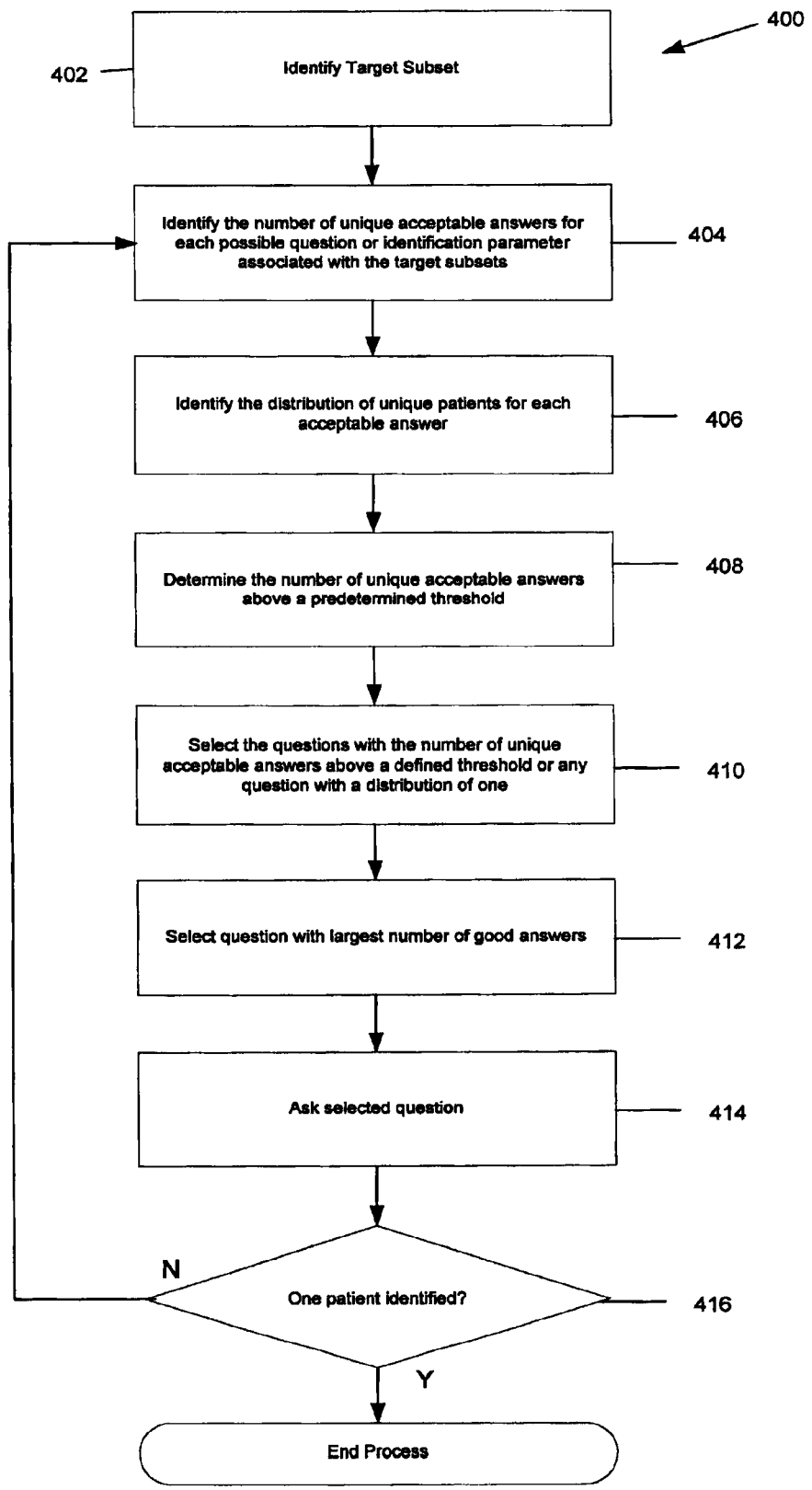
FIG. 22 is a flow chart illustrating a patient look-up process that provides patient check in and access to health records in accordance with an alternate embodiment of the invention.

Referring now to FIG. 22, in an alternate embodiment of the invention, the kiosk 26a can be used to find a patient, guardian, or dependent in the database using a patient "look-up" system that identifies a particular patient based on personal identification data input by the kiosk operator. Although, for simplicity, the system will be described below with reference to identifying a patient, it will be apparent the system can also be used to identify a guardian, or an accountholder in the database, and that it is not necessary that the identified individual be a patient. It will also be apparent that the described system can be used in lieu of other forms of identification, or in combination with a patient identifier such as a credit card, driver's license, insurance card, or other token. In the process described below, a probability calculation is used to limit the amount of data that must be input by a user. The probability is calculated based on an analysis of the data in the database, and therefore increases both the security and efficiency of an automated patient identification process.

Figure 24:
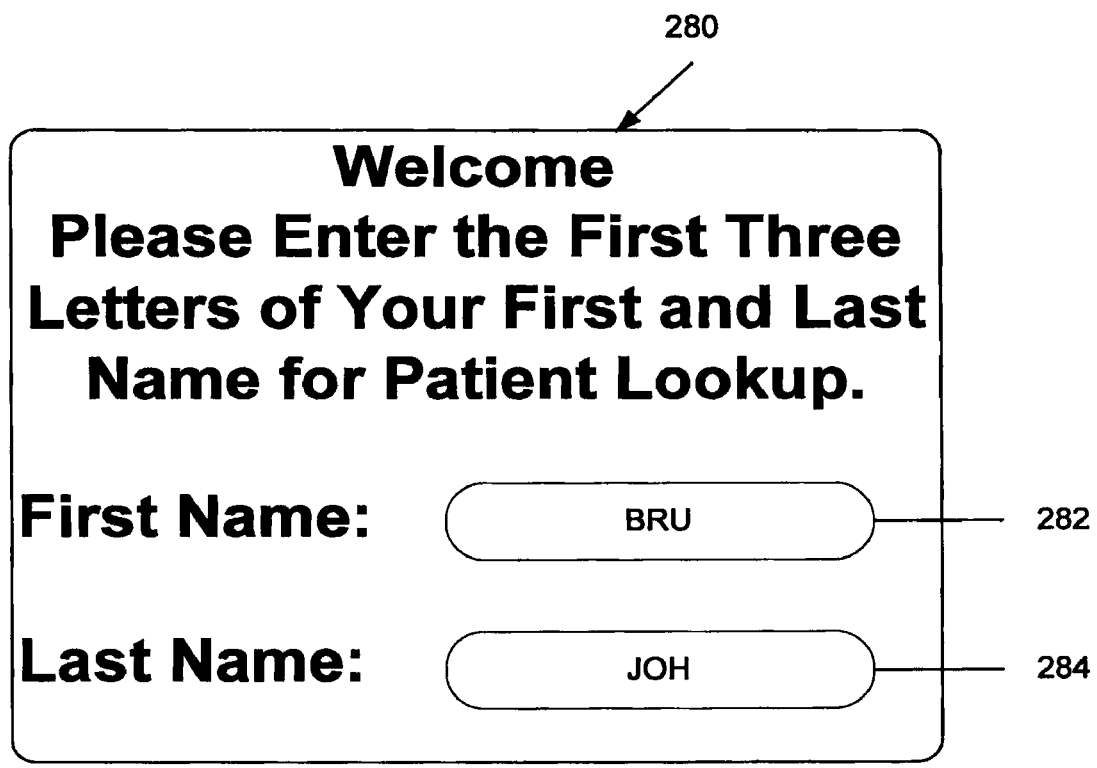
FIG. 24 is a screen shot illustrating acquisition of patient identification data for the patient look-up of FIG. 22.

Referring still to FIG. 22, in initial step 402 of patient look-up process 400, a target subset of patients or patient data is initially identified. The target subset can be determined based on patient identifying data, such as a name or a portion of the name of the patient, or a social security number or a portion of a social security number provided by the patient. Alternatively, the subset could be determined based on a known list of patients that have appointments on the specific day that the kiosk is being used. In any case, the purpose of this step is to narrow the set of patient data that must be evaluated to determine the identity of the patient using the kiosk 26a. Referring now also to FIG. 24, an exemplary screen shot is shown. Here, in screen shot 280, the kiosk 26a prompts the patient to enter the first three letters of his or her first and last name in data entry blocks 282 and 284. As shown here by way of example, the patient enters the first three letters "Bru" in data block 282 and the first three letters "Joh" in block 284.

Referring now also to FIG. 23 a patient look-up data base 290 is shown including patient identifying data, here shown as a patient name 292, birth date 293, social security number 294, phone number 295, and zip code 296. As shown here by way of example, there are four patients whose names are retrieved based on the data entered into the screen shot 280: Bruce Johnson, who lives at 555 Maple Drive and has a birth date of Jul. 31, 1960; Bruce Johnson who also lives at 555 Maple Drive and has a birth date of May 1, 1937; Bruno Johnsrud, who lives at 1222 North St. and was born on Jun. 3, 1979 and Bruce Johnstone, of 777 Oak Court, born on Jun. 4, 1979. To narrow the identity of the patient, the process 400 continues to process block 404 to begin the process of determining the best next question to ask.

Referring again to FIG. 22, in process block 404, the process 400 evaluates the data in the database 290 to identify the number of unique acceptable values or answers for each identification parameter in the database subset identified in process block 402. Referring again to FIG. 23, here, for example, there are four sets of identification parameters shown: birth date, social security number, phone number, and zip code. The birth date, moreover, can be parsed into individual comparable segments consisting of a month, a date, and a year. Each of these columns, and each segment of the parsed birth date data, represents a potential question for the user, the answer to which helps to further narrow the potential list of patients, and to eventually identify the patient. In process block 404, the system evaluates the data in each individual column to determine the number of unique acceptable answers. In the limited example shown here, for example, there are three unique acceptable answers to a question requiring a patient to identify a zip code or telephone number, two answers in the social security number column, and four unique answers or values in the date of birth column. This data is used by the process 400 to determine which data will most quickly narrow the field of patients to a single, unique patient. If the birth date column is further broken down by month, date, and year, the number of possibilities decreases.

In process block 406, the process 400 calculates the distribution of unique patients associated with each acceptable answer. Using the limited example above of FIG. 23, there are two patients associated with the zip code 54321, and one patient each associated with the other two zip codes. In step 408, the process 400 determines the number of questions having unique acceptable answers above a threshold value, where the threshold can be a fixed number, a percentage, or a ranking relative to other questions.

Subsequently, in step 410, the process 400 selects the question with the largest number of "good answers", where a good answer is an answer that has fewer than a defined threshold number of patients associated with it. By way of example, a question may have ten acceptable answers, as determined in step 404. In step 406, it is determined that three of the ten acceptable answers have ten or more patients associated with the answer. Five have six or more patients, and two have three or fewer patients associated with each answer. In this example, there are two good answers, because these answers filter the field to three or fewer patients, thereby limiting the number of additional questions that would be required to identify the patient. In step 412, the question with the largest number of good answers is selected, and in process block 414, that question is displayed to the user. Subsequently, the process 400 determines whether a patient is uniquely identified in block 416. If the patient is not uniquely identified by the response to the question, the process 400 returns to step 404. The process continues until a specific patient is identified, or until it becomes clear that the patient cannot be identified. At this point, the patient can be directed to a receptionist.

Referring again to FIG. 24 and now also FIG. 25 through FIG. 28, a series of example screen shots 280, 300, 304, 308, and 312 are shown in which the patient at the kiosk is asked to provide personal data to verify identity. Here, the questions actually presented to a patient will be filtered as described above.

Figure 25:
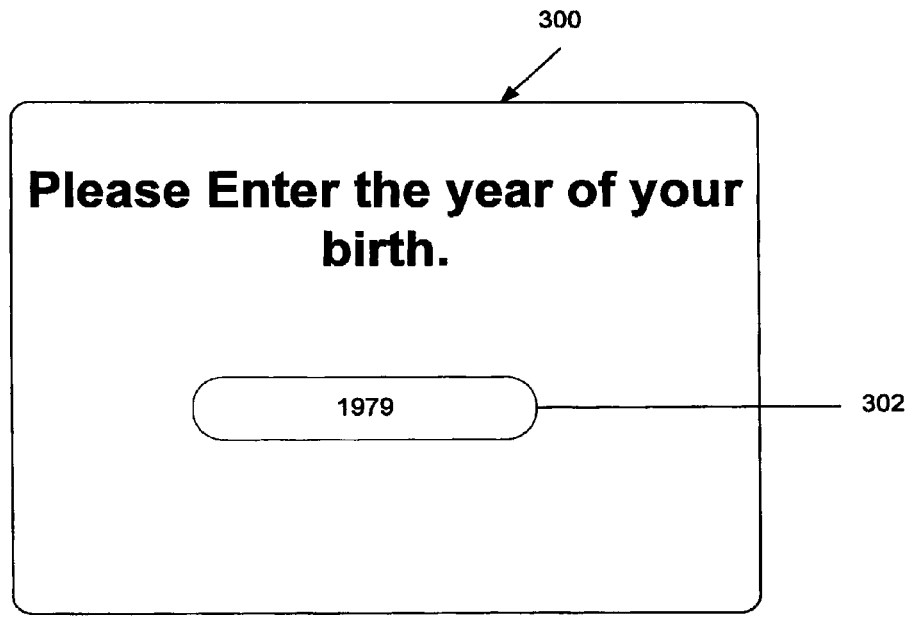
FIG. 25 is another screen shot illustrating acquisition of patient identification data for the patient look-up of FIG. 22.
Figure 26:
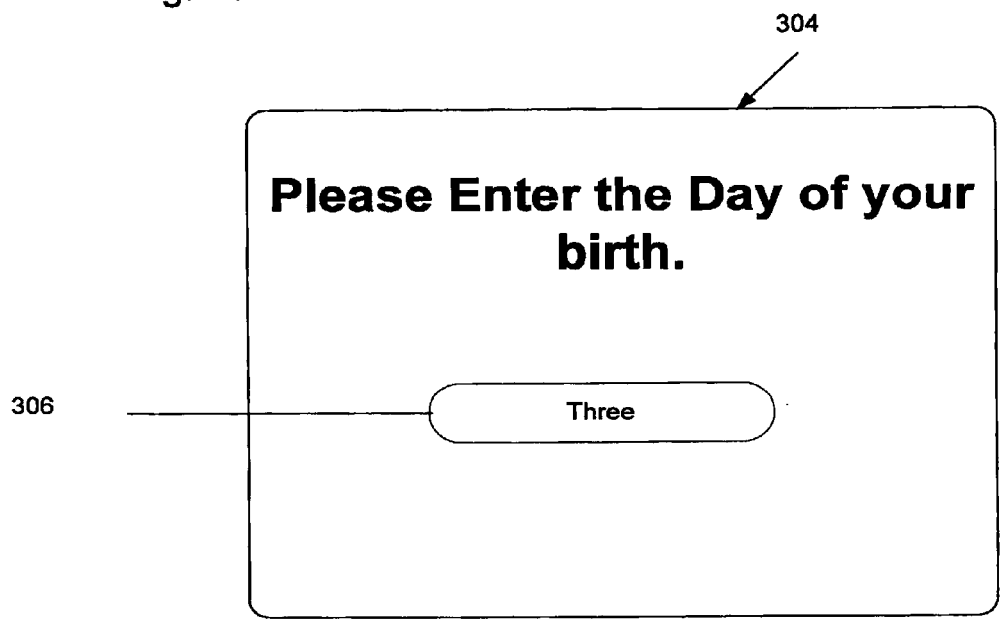
FIG. 26 is another screen shot illustrating acquisition of patient identification data for the patient look-up of FIG. 22.
Figure 27:
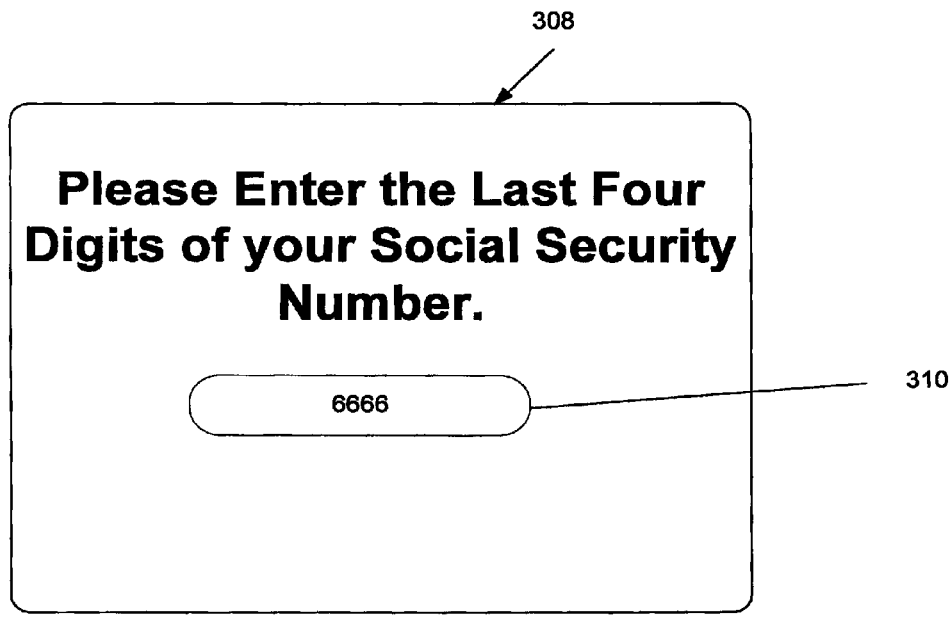
FIG. 27 is yet another screen shot illustrating acquisition of patient identification data for the patient look-up of FIG. 22.
Figure 28:
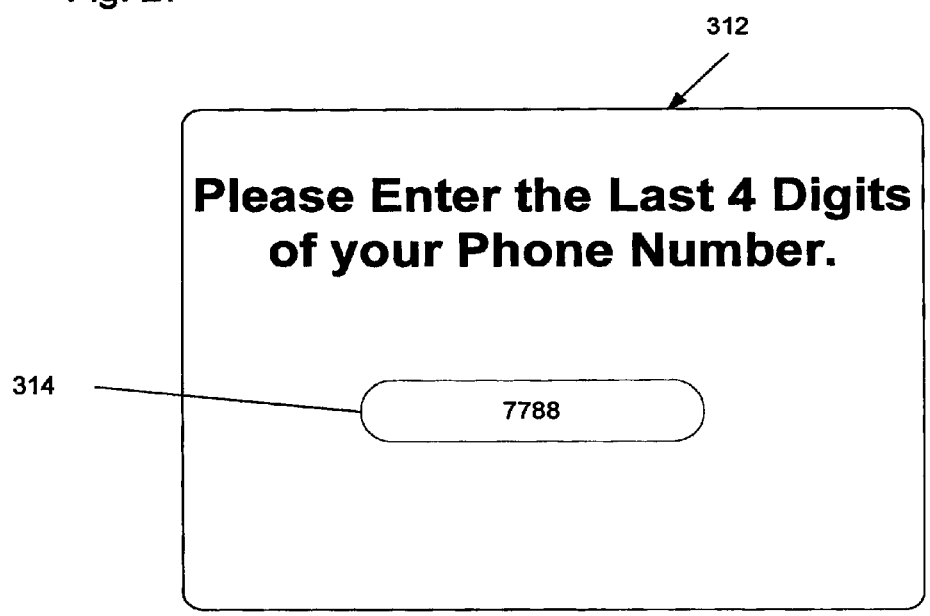
FIG. 28 is still screen shot illustrating acquisition of patient identification data for the patient look-up of FIG. 22.

Referring first to FIG. 25, in screen shot 300, the patient is prompted to enter the year of his or her birth. As shown here, a data block 302 is provided for entry of the data, and the patient enters 1979, which, referring also to FIG. 23, narrows the identity of the patient to either BrLino Johnsrud or Bruce Johnstone. In FIG. 26, in screen shot 304, the kiosk 26a requests day of his or her birth, and the patient here enters the number three into data block 306. Based on this data, the system can determine that the patient is Bruno Johnsrud. In some applications, therefore, it would be possible to stop acquiring data at this point. However, if the patient is not uniquely identified, or if it is desirable to verify the identity of the patient, the kiosk can move on to the screen 308 of FIG. 27, which prompts the user to identify the last four digits of his or her social security number, and in screen shot 312 of FIG. 28, the last four digits of his or her telephone number. Although not shown here, it will be apparent that the zip code of column 290, address, or other data could also be acquired to determine the identify of the patient.

Although described above for purposes of identifying a patient, as noted above, it will be apparent that the patient look-up system described above can also be used to identify a guardian, who can then be given access to the associated records of dependents, as shown, for example, in the database of FIG. 11. In this application, personal identification of the dependent can also be requested, as described above.

Although the system has been described above as including data entry blocks, in alternative embodiments of the invention, a touch screen could be used and the data for entry provided on screen. Thus, for example, in the screen shot 280 of FIG. 22, an alphabet can be provided on the screen, and the user prompted to select the appropriate letters from the display screen. In the remaining screens, a series of digits between 0 and 9 can be shown. Alternatively, a list of, for example, the birth years of column 293 in FIG. 23 could all be displayed, preferably with a series of random years that are not associated with any of the identified patients, again to limit the probability of identity theft or fraud, and to retain compliance with federal regulations.

Furthermore, although the system has been described above with reference to an automated patient check-in system, and specifically a kiosk system, it will be apparent that the identification methods described above can also be applied in other applications, and that the inventive concepts of the present invention are not limited to use in kiosks. Additionally, communications between a patient and the patient check-in system 10a can be provided using wireless personal communication devices 743 (FIG. 1). A user can, for example, submit credit card identification data wirelessly from the device 743 rather than inserting a card into a card reader as described above. Identifying data for a driver's license, insurance account, or other data could also be transmitted rather than entered through a kiosk.

Additionally, although specific screen shots are described above both for a receptionist computer 950 and a kiosk 26a, it will be apparent that the screen shots are exemplary only, and that the icons, data entry screens, and informational screens shown are not intended to limit the invention. The data accessible through these systems is limited only by what is available in the associated databases, and access rights associated with the user accessing the database.

One or more specific embodiments of the present invention have been described above. It should be appreciated that in the development of any such actual implementation, as in any engineering or design project, numerous implementation-specific decisions must be made to achieve the developers' specific goals, such as compliance with system-related and business related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Thus, the invention is to cover all modifications, equivalents, and alternatives falling within the spirit and scope of the invention as defined by the following appended claims. To apprise the public of the scope of this invention, the following claims are made:

The invention claimed is:

1. A memory for use in a computer system in a health care facility to provide access to health care services for a first and a second dependent medical patient by a corresponding first and second guardian through a credit account shared by the first and second guardians, the memory comprising:
    a patient database including an account data structure associating the shared credit account with the first and second dependent medical patients;
    a first dependent data structure correlating a first guardian identifier identifying the first guardian with the first dependent medical patient; and
    a second dependent data structure correlating a second guardian identifier identifying the second guardian with the second dependent medical patient, wherein the computer system is programmed to correlate the first guardian identifier with the first dependent medical patient in the database and to provide the first guardian access to at least a portion of the health care database to process health care services for the first dependent medical patient, while preventing access to the second dependent medical patient when the first guardian provides data identifying the credit account.

2. The memory as recited in claim 1, wherein at least one of the first guardian identifiers comprises a database key constructed from account data identifying the credit account and a personal identifier associated with a credit card.

3. The memory as recited in claim 2, wherein the personal identifier comprises at least one of a name, a card verification code, and a card id corresponding to a credit card held by the first or second guardian.

4. The memory as recited in claim 1, wherein at least one of the first and second guardians is a patient in the patient database.

5. The memory as recited in claim 1, wherein at least one of the first and second Guardians is not a patient in the patient database.

6. The memory as recited in claim 1, further comprising a third dependent data structure, the third dependent data structure correlating the first guardian identifier and the second guardian identifier with a third dependent, wherein the computer system is further programmed to provide both the first guardian and the second guardian access to at least a portion of the health care database to process health care services for the third dependent medical patient when either the first or the second guardian provides data identifying the credit account.

7. A computer system for use in a health care facility to allow a first guardian of a first dependent medical patient and a second guardian of a second dependent medical patient to access health care services for the corresponding first and second dependent medical patient using corresponding first and second identifiers associated with a credit account shared by the first and second guardians, respectively, the data access system comprising:
- a health care computer network;
- a health care database including a patient database, and a data structure associating an account identifier with a credit account shared by the first and second guardian, a first guardian identifier corresponding to the shared account and the first guardian, and a second guardian identifier corresponding to the shared account and the second guardian, at least a first dependent medical patient associated with the first guardian in the data structure, and at least a second dependent medical patient associated with the second guardian in the data structure; and
- a reader device connected to the computer network for reading the first and second guardian identifiers when presented, wherein the health care computer network is programmed to correlate the first guardian identifier with the first dependent medical patient in the database and the second guardian identifier with the second dependent medical patient, respectively, and to provide the first guardian access to at least a portion of the health care database to process health care services for the first dependent medical patient, and the second guardian access to at least a portion of the health care database to process health care services for the second dependent medical patient.

8. The computer system as recited in claim 7, wherein at least one of the first and second guardian identifiers comprises a representation of the account number combined with at least one of a name, a card id, and a card verification code.

9. The computer system as recited in claim 7, wherein the account identifier comprises a credit card.

10. The computer system as recited in claim 7, wherein the account identifier comprises at least one of a credit card, an RFID tag, and a barcode.

11. The computer system as recited in claim 7, wherein the first and second guardian identifiers comprise at least one of a driver's license, a health insurance card, and a biometric identifier.

12. The computer system as recited in claim 7, wherein the first and second guardian identifiers comprise at least one of an active memory storage device and a passive memory storage device.

13. The computer system as recited in claim 7, wherein the health care computer network is programmed to prevent access to the first guardian to process health care services for the second dependent medical patient.

14. The computer system as recited in claim 7, wherein the health care computer network is programmed to prevent access to the second guardian to process health care services for the first dependent medical patient.

15. The computer system as recited in claim 7, wherein at least one of the first and second guardians is a patient identified in the patient database.

16. The computer system as recited in claim 7, wherein at least one of the first and second guardians is not a patient identified in the patient database.

17. The data access system as recited in claim 7, wherein the database correlates a plurality of dependent medical patients with at least one of the first and second guardian identifiers.

18. A computerized method for associating a first and a second guardian with corresponding first and second dependent medical patients to provide access to health care data for the dependents through a health care computer network when using a shared credit account of the first and second guardians, the method comprising the following steps:
- prompting the first guardian to register account data for the shared credit account in a healthcare database, the account data including at least one of an account number and a first guardian identifier;
- prompting the second guardian to register credit account data for the shared account in the healthcare database, the account data including at least one of an account number and a second guardian identifier; and
- associating a first dependent medical patient of the first guardian in a database with the account number and the first guardian identifier; and
- associating a second dependent medical patient of the second guardian in a database with the account number and the identifier of the second guardian, wherein when the first guardian uses the account as identification, the first guardian is provided access to process health care services for the first dependent medical patient and prevented from accessing health care services for the second dependent medical patient, and when the second guardian uses the account as identification, the second guardian is provided access to process health care services for the second dependent medical patient and prevented from accessing health care services for the first dependent medical patient.

19. The method as recited in claim 18, further comprising the step of constructing a database key to identify at least one of the first and second guardians from the shared account and a personal identifier associated with the account.

20. The method as recited in claim 19, wherein the personal identifier associated with the account comprises at least one of a name, a card id, or a card verification code.

21. The method as recited in claim 18, further comprising the steps of producing a first unique identifier as a combination of the account number and the identifier of the first guardian and a second unique identifier as a combination of the account number and the identifier of the second guardian.

22. The method as recited in claim 18, wherein the shared account is identified by a readable identifier including at least one of an active memory storage device, a passive memory storage device, or an optical encoding device.

23. The method as recited in claim 18, wherein the first and second guardian identifiers are machine-readable, and further comprising the step of providing the first and second guardian identifiers to a reader, wherein the reader reads the identifier to allow access for the guardian to process health care services.

24. The method as recited in claim 18, further comprising the step of associating at least one dependent of the first guardian with the personal identifier of the second guardian when the corresponding dependent is also a dependent of the second guardian.

25. The method as recited in claim 18, further comprising the step of associating at least one dependent of the second guardian with the first personal identifier of the first guardian when the corresponding dependent is also a dependent of the first guardian.

26. The method as recited in claim 18, wherein at least one of the first and second guardians is a patient registered in the healthcare database.

27. The method as recited in claim 18, wherein at least one of the first and second guardians is not a patient registered in the healthcare database.

* * * * *